United States Patent [19]
Lydon et al.

[11] Patent Number: 5,906,601
[45] Date of Patent: May 25, 1999

[54] USE OF AN ADHESIVE COMPOSITION IN THE MANUFACTURE OF A WOUND DRESSING

[75] Inventors: Michael James Lydon, Flintshire; Michael J. Waring, Wirral; Stephen Thomas, Mid Glamorgan, all of United Kingdom

[73] Assignee: Bristol-Myers Squibb Company, New York, N.Y.

[21] Appl. No.: 08/739,661

[22] Filed: Oct. 31, 1996

[30] Foreign Application Priority Data

Nov. 1, 1995 [GB] United Kingdom .................. 9522313

[51] Int. Cl.$^6$ .................................................. A61M 35/00
[52] U.S. Cl. .............................................................. 604/290
[58] Field of Search ...................... 604/290, 304, 604/307, 306, 336, 43, 54, 56; 424/443–448; 602/42, 43, 44, 48, 54

[56] References Cited

U.S. PATENT DOCUMENTS

| 4,393,080 | 7/1983 | Pawelchak et al. ................. 604/336 |
| 4,743,499 | 5/1988 | Volke .................................. 428/317.3 |
| 4,867,748 | 9/1989 | Samuelsen .............................. 604/336 |
| 4,952,618 | 8/1990 | Olsen ......................................... 524/17 |
| 5,571,080 | 11/1996 | Jensen ................................... 604/336 |
| 5,591,820 | 1/1997 | Kydonieus et al. ....................... 528/76 |
| 5,633,010 | 5/1997 | Chen ....................................... 424/448 |

*Primary Examiner*—John G. Weiss
*Assistant Examiner*—David J. Cho
*Attorney, Agent, or Firm*—John M. Kilcoyne; Theodore R. Furman, Jr.

[57] ABSTRACT

This invention relates to the use of an adhesive composition for the preparation of a wound dressing, or part of a wound dressing, for treating wounds by reducing the volume of exudate produced by the wound.

9 Claims, No Drawings

USE OF AN ADHESIVE COMPOSITION IN THE MANUFACTURE OF A WOUND DRESSING

The invention relates to the use of an adhesive composition for the preparation of a medicament and in particular a wound dressing or part thereof.

The use of wound dressings capable of forming a substantially fluid tight seal with skin surrounding a wound for the treatment of the wound is well known in the art. For example EP-B-92999 discloses a three layer dressing which has as a wound and skin contacting layer, a blend comprising hydrocolloid and polyisobutylene. Similar dressings are disclosed in EP-B-190814, EP-B-130061 and EP-A-621042 and are used particularly in the treatment of recalcitrant skin damage such as ulcers, or of burns and donor sites.

A problem associated with skin damage and particularly ulcers is that such wounds can produce significant amounts of exudate. The management of the exudate is a problem for both the patient and the healthcare professional treating the patient. Improvements in the management of wound exudate are thus always sought. In the past, solutions to the problem of exudate management have focused on increasing the absorbency of dressings in order to absorb the exudate.

Surprisingly we have now found that it is actually possible to influence exudate production and reduce the volume of exudate produced by a wound by use of a wound dressing. Reducing the volume of exudate produced by the wound enhances patient comfort and can enhance healing by reducing the frequency of dressing changes thereby reducing disturbance to the wound. Accordingly the invention provides the use of an adhesive composition for the preparation of a wound dressing or part of a wound dressing, for use in the treatment of wounds by reduction of the volume of exudate produced by the wound.

Whilst not wishing to be bound by theory we believe that the reduction in exudate is caused by pressure on the wound generated by the closed environment produced by the wound dressing. The pressure is not externally applied pressure as would for instance be applied by an external bandage but pressure generated by exudate build-up under the dressing creating a back pressure. Accordingly, in another aspect, the invention provides the use of an adhesive composition in the manufacture of a wound dressing for use in the treatment of wounds by creating pressure on the wound bed and thereby reducing the volume of exudate.

Preferably the adhesive composition of the wound dressing produces a seal with the intact skin surrounding the wound. Accordingly the invention provides the use of a composition capable of forming a seal against leakage of exudate on skin surrounding a wound in the manufacture of a wound dressing for use in the treatment of wounds by reducing the volume of exudate produced by the wound.

Preferably the wound dressing reduces the volume of exudate produced by the wound by between 1% and 50% of control values.

More preferably the wound dressing reduces the volume of exudate produced by the wound by between 10% and 50%. More preferably the wound dressing reduces the volume of exudate produced by the wound by at least 20%, more preferably at least 30%.

In general it is desirable for the composition to be of such a nature and structure that it retains its integrity on prolonged contact with wound exudate.

Preferably the adhesive composition comprises a homogeneous blend of one or more water soluble hydrocolloids and one or more low molecular weight polyisobutylenes such as are described in EP-B-92999 incorporated herein by reference. For example, the adhesive composition may comprise a homogeneous blend on a percent weight basis of from 35% to 65% hydrocolloid and 35% to 65% of polyisobutylene. The water soluble hydrocolloids may be selected from sodium carboxymethylcellulose, pectin, gelatin, guar gum, locust bean gum, gum karaya, and mixtures therof. The polyisobutylenes may be selected from low molecular weight polyisobutylenes having a viscosity average molecular weight of from 36,000 to 58,000 (Florey).

Alternatively the adhesive composition may comprise a homogeneous blend of one or more hydrocolloids, one or more low molecular weight polyisobutylenes, one or more styrene block copolymers, mineral oil, butyl rubber, a tackifier and small amounts of optional components. By selection of specific ranges of the amounts of the above listed components, adhesive compositions may be prepared having good adhesion to the skin and strechability. Such compositions and the preparation thereof are disclosed in EP-B-130061 incorporated herein by reference. For example, the adhesive composition may comprise a homogeneous blend on a percent weight basis of from 5% to 30% of a blend of one or more polyisobutylenes and butyl rubber, from 3% to 20% by weight of one or more styrene radial or block type copolymers, from 8% to 40% by weight of mineral oil, from 15% to 65% by weight of one or more water soluble hydrocolloids, optionally up to 15% by weight of one or more water swellable cohesive strengthening agents and from 7.5% to 15% by weight of a tackifier. In a particularly preferred embodiment of the present invention the adhesive composition comprises:

| Ingredient | % by weight |
|---|---|
| Polyisobutylene(Vistanex LMMH) | 8 |
| Pectin | 15 |
| Gelatin | 15 |
| Sodium carboxymethylcellulose | 15 |
| Mineral oil | 13.5 |
| S-I-S copolymer (Kraton 1107) | 6.75 |
| Tackifier | 10 |
| Antioxidant | 0.50 |
| Butyl rubber (Grade 065) | 16.25 |

The composition may also comprise reinforcing fibres such as described in EP-B-130061 and EP-A-621042 to aid in the maintenance of the structural integrity of the dressing. Preferably the reinforcing fibres are present at a level of from 2% to 10% by weight of the adhesive composition.

The composition may be in the form of a layer of the island type where different regions of the adhesive layer have different properties. For example the adhesive layer could comprise a central zone of swellable material backed and surrounded by a more rigid adhesive.

The invention will now be illustrated by the following non-limiting examples.

EXAMPLE 1

A method was devised to compare the amount of exudate produced beneath an intact wound dressing and that produced by the same wound covered with an identical dressing perforated to allow fluid to pass into an external absorbent layer. The dressings used were hydrocolloid dressings and in particular Improved Formulation Granuflex™ ex ConvaTec.

Perforated dressings were prepared immediately prior to application as follows:

A tracing of the wound was made on a transparent plastic sheet from which the outline of the wound was cut out and discarded. The resulting template was then used to mark out the margin of the wound upon the back of a 15 cm×15 cm sheet of (Improved Formulation Granuflex™). Within the marked area, five holes were produced using a 4 mm biopsy punch and the dressing was applied to the wound.

A sterile nonwoven gauze swab was applied to the back of the perforated dressing over the perforations and retained in position with a sheet of adhesive film to prevent evaporative loss. Steridrape™ ex 3M Healthcare was selected for this purpose because of its low moisture vapour transmission rate. For wounds dressed with an intact dressing, the process was repeated, omitting the perforating of the (Improved Formulation Granuflex™).

All the components used to dress a wound were supplied sterile in a sealed outer plastic bag of known weight. Following application of the dressing, the biopsy punch and discs of dressing together with all packaging and release papers were returned to the plastic bag and reweighed. From these two values the weight of the dressing applied to a wound could be calculated.

At the time of dressing change, the Improved Formulation Granuflex™ was removed from the wound together with swab and film and placed in a second bag of known weight. Any liquid remaining upon the surface of the wound was carefully removed with previously weighed sterile swabs that were also placed in the second bag which was subsequently reweighed. The combined weight of the dressing and exudate was then calculated by difference, from which the weight of exudate was determined by subtracting the weight of the original dressing calculated previously.

Because it was assumed that exudate production would vary from patient to patient, both dressing systems were applied alternately to each patient until a total of 10 results were obtained. In this way each patient acted as their own control. Patients were randomised to determine which form of dressing they would receive first.

The area of each wound was determined at intervals by a weighing method using the tracings made on transparent film. Appropriate compression therapy was provided for all patients.

Ten patients, were selected from males and females of over 18 years of age with leg ulcers 4–10 cm in width. The interval between dressing changes for each patient was determined by the investigator based upon an initial assessment of the wound and their subjective estimate of the amount of exudate that was anticipated. Once that time period was selected however it remained constant for that patient for the duration of the study.

Table 1 shows details concerning the wounds included in the method.

TABLE 1

| Patient | | | Wound area cm² | |
| No | Sex | Wound Location | Initial | Final |
| --- | --- | --- | --- | --- |
| 1 | M | Ankle (medial) | 17.7 | 13.7 |
| 2 | F | Ankle (medial) | 24.5 | 25.4 |
| 3 | F | Gaiter (anterior) | 11.8 | 0.5 |
| 4 | F | Gaiter (lateral) | 12.0 | 7.9 |
| 5 | F | Ankle (posterior) | 39.8 | 31.3 |
| 6 | F | Gaiter (medial) | 10.5 | 7.7 |
| 7 | M | Ankle (medial) | 7.4 | 5.2 |
| 8 | F | Calf (posterior) | 13.0 | 10.3 |

TABLE 1-continued

| Patient | | | Wound area cm² | |
| No | Sex | Wound Location | Initial | Final |
| --- | --- | --- | --- | --- |
| 9 | M | Gaiter (medial) | 33.9 | 43.6 |
| 10 | M | Gaiter (anterior) | 9.4 | 4.4 |

Table 2 shows exudate production for each patient.

TABLE 2

| | Change | Mean Exudate Weight (grams†) | | Mean Exudate Weight (g/cm²/24hrs†) | |
| Patient | hours | Intact | Perforated | Intact | Perforated |
| --- | --- | --- | --- | --- | --- |
| 1 | 48 | 13.5 | 27.5 | 0.43 | 0.9*** |
| 2 | 72 | 14.3 | 33.6 | 0.19 | 0.45*** |
| 3 | 72 | 7.7 | 6.7 | 0.36 | 0.5(ns) |
| 4 | 48 | 7.5 | 10.5 | 0.39 | 0.52* |
| 5 | 48 | 15.0 | 29.5 | 0.21 | 0.41*** |
| 6 | 24 | 5.1 | 4.3 | 0.58 | 0.48* |
| 7 | 72 | 15.8 | 21.9 | 0.83 | 1.2** |
| 8 | 48 | 6.8 | 10.4 | 0.29 | 0.44* |
| 9 | 24 | 8.0 | 18.4 | 0.2 | 0.47*** |
| 10 | 48 | 12.6 | 12.7 | 0.82 | 0.87(ns) |

†each result represents the mean of five readings
ns = not significant
* = p < 0.05 significant (95%)
** = p < 0.01 highly significant (99%)
*** = p < 0.001 extremely significant (99.9%)

The results show that in seven out of ten patients the amount of exudate produced beneath the perforated dressing was greater than that produced beneath the intact dressing. This difference was significant at the 95% level.

An analysis of variance performed on the data showed that the mean weight of exudate from all wounds dressed with intact dressings ($0.4330 \pm 0.2416$) was lower than that from the wounds dressed with perforated dressings ($0.6273 \pm 0.2895$). This result is highly significant ($p<0.01$).

Patient 6 showed a reverse pattern probably because of the 24 hour dressing change regimen used for this patient which probably did not allow any pressure build up to occur.

We claim:

1. A method of treating wounds comprising forming a seal against leakage of exudate, on skin surrounding a wound, with an adhesive composition, and permitting the accumulation of exudate under the adhesive to create a back pressure, thereby inhibiting further exudate production.

2. The method of claim 1 wherein the adhesive composition comprises a homogeneous blend of hydrocolloid and polyisobutylene.

3. The method of claim 1 wherein the adhesive composition comprises a homogeneous blend on a percent weight basis of from 35% to 65% hydrocolloid and 35% to 65% of polyisobutylene.

4. The method of claim 1 wherein the adhesive composition comprises a homogeneous blend on a percent weight basis of from 5% to 30% of a blend of one or more polyisobutylenes and butyl rubber, from 3% to 20% by weight of one or more styrene radial or block type copolymers, from 8% to 40% by weight of mineral oil, from 15% to 65% by weight of one or more water soluble hydrocolloids, optionally up to 15% by weight of one or more water swellable cohesive strengthening agents and from 7.5% to 15% by weight of a tackifier.

5. The method of claim 4 wherein the adhesive composition further comprises from between 2% and 10% by weight of reinforcing fibers.

6. The method of claim 5 wherein the reinforcing fibers are cellulose fibers.

7. The method of claim 1 wherein the dressing reduces the volume of exudate produced by the wound by between 1 and 50%.

8. The method of claim 1 wherein the adhesive composition is in the form of an adhesive layer of the island type with different regions of the adhesive layer having different properties.

9. The method of claim 8 wherein the adhesive layer comprises a central zone of swellable material backed and surrounded by a more rigid adhesive.

* * * * *